(12) United States Patent
Delanef et al.

(10) Patent No.: US 8,206,668 B2
(45) Date of Patent: Jun. 26, 2012

(54) APPARATUSES FOR PRODUCING A GAS CHARGED WITH A VOLATILE COMPOUND

(75) Inventors: Marie-Laure Delanef, Artaix (FR); Jean-Michel Collaudin, Saint Germain en Brionnais (FR)

(73) Assignee: Holiste Laboratoires et Developpment, Artaix (FR)

( * ) Notice: Subject to any disclaimer, the term of this patent is extended or adjusted under 35 U.S.C. 154(b) by 519 days.

(21) Appl. No.: 12/593,169

(22) PCT Filed: Mar. 19, 2008

(86) PCT No.: PCT/FR2008/000358
§ 371 (c)(1),
(2), (4) Date: Sep. 25, 2009

(87) PCT Pub. No.: WO2008/135651
PCT Pub. Date: Nov. 13, 2008

(65) Prior Publication Data
US 2010/0086449 A1    Apr. 8, 2010

(30) Foreign Application Priority Data

Mar. 26, 2007  (FR) ...................................... 07 02162

(51) Int. Cl.
  *B01J 8/04*    (2006.01)
  *B01J 10/00*   (2006.01)
(52) U.S. Cl. ......... 422/630; 422/644; 422/645; 422/649
(58) Field of Classification Search .................. 422/630, 422/644–645, 649
See application file for complete search history.

(56) References Cited

U.S. PATENT DOCUMENTS 4,282,187 A * 8/1981 Corbett et al. ................. 422/610
4,568,522 A * 2/1986 Corbett .......................... 422/186

FOREIGN PATENT DOCUMENTS

| DE | 3049244 | 7/1982 |
| EP | 0346552 | 12/1989 |
| FR | 2654273 | 5/1991 |
| GB | 512586  | 9/1939 |

OTHER PUBLICATIONS

International Search Report dated Nov. 24, 2008, in PCT application.

* cited by examiner

*Primary Examiner* — Walter D Griffin
*Assistant Examiner* — Christopher Vandeusen
(74) *Attorney, Agent, or Firm* — Young & Thompson

(57) ABSTRACT

The apparatus of the invention is essentially characterized by the fact that it includes a fluid-flow duct (10) having an inlet (11) and an outlet (12), and mounted in succession in series in the duct (10): a suction fan (20) for sucking in a carrier gas available at the inlet (11) and for discharging it towards the outlet (12); a bubbler (30) suitable for causing the carrier gas to pass through a volatile liquid (31) contained in the bubbler so as to obtain a stream of carrier gas (33) charged with vapor of the liquid; a device (40) for fractioning the charged stream to deliver a charged stream in fractioned form; and a member (50) for treating the fractioned charged stream to impart a determined quality thereto before it is ejected from the outlet (12) of the duct (10). The invention is applicable in particular to producing a gas charged with a volatile compound, in particular for inhalation.

17 Claims, 3 Drawing Sheets

APPARATUSES FOR PRODUCING A GAS CHARGED WITH A VOLATILE COMPOUND

The present invention relates to apparatuses for producing gas charged with a volatile compound, such as, for example, but not exclusively, an organic derivative of oxonium, and more particularly oxonium terpene peroxide, e.g. for the purpose of inhaling it.

An apparatus is known, in particular from EP-A-0 346 552, for producing oxonium terpene peroxides that is characterized by the fact that it is initially raised to a relatively high temperature, and then cooled by a stream of gas charged with vapors of oleoresin terpene derivatives to a temperature lying in the range 35° C. to 280° C.

That apparatus includes an electric arc generator and/or an ultraviolet radiation radiator and/or, most advantageously, a combination of both those generators. A flow of gas is thus produced that is charged with oleoresin terpene derivatives and that is subjected to the action of an electric arc and/or ultraviolet radiation. It is also possible to subject the charged gas to the action of a heat generator such as an electrical resistance.

Another apparatus is known such as that described in GB-A-512 586 that has a plurality of jars or chambers connected in series and positioned relative to one another by being distributed on a helix or the like in such a manner as to replace their linear space requirement (see FIG. 5) by a wound space requirement (see FIGS. 1 to 4). Unfortunately, that arrangement does not lead to a reduction in the total space occupied, but merely transforms it, and in addition it does not make the apparatus pleasing in appearance.

Thus, an object of the present invention is to provide an apparatus for producing gas charged with a volatile compound, such as, for example but not exclusively, an organic derivative of oxonium, and more particularly oxonium terpene peroxide, which compound is suitable for being inhaled, and which apparatus mitigates to a large extent the above-mentioned drawbacks of similar apparatuses in the prior art, by producing a structure that is much more compact and attractive in appearance than similar apparatuses in the prior art, and while also making the apparatus easier to use.

More precisely, the present invention provides an apparatus for producing a gas charged with a volatile compound, as defined in accompanying claim 1.

Other characteristics and advantages of the invention appear from the following description given with reference to purely illustrative and non-limiting accompanying drawings, in which.

It is initially specified that, in the figures, the same references are used to designate the same elements, regardless of the figure in which they appear and regardless of the way in which the elements are shown.

Figure 1:
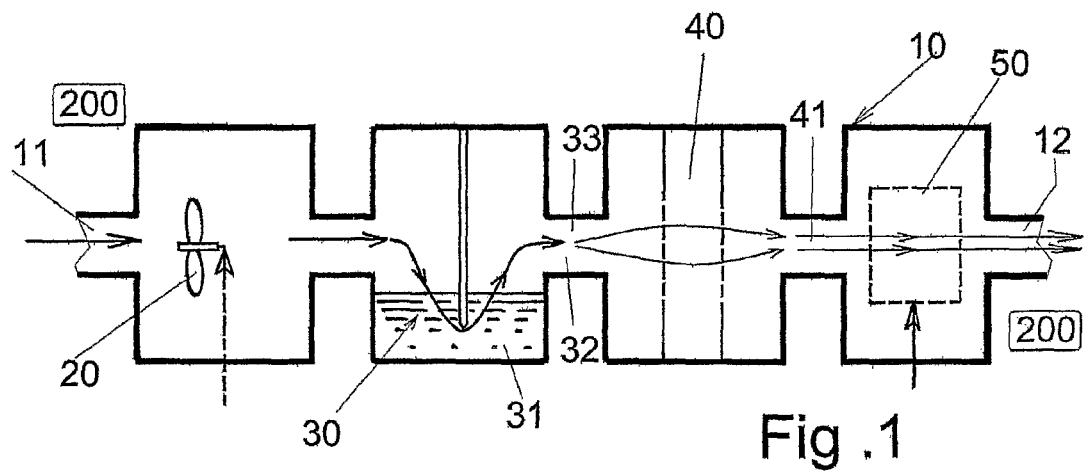
FIG. 1 is a functional block diagram of the apparatus of the invention for producing a gas charged with a volatile compound.

With reference more particularly to FIG. 1, which is in the form of a block diagram, the apparatus of the invention for producing a gas charged with a volatile compound, e.g. an organic derivative of oxonium and more particularly oxonium terpene peroxide, in particular for the purpose of inhalation, comprises a fluid-flow duct 10 with an inlet 11 and an outlet 12.

Still more particularly with reference to FIG. 1, the apparatus further comprises, connected in succession in series along the fluid-flow duct 10 between its inlet 11 and its outlet 12: a suction fan 20 for sucking in a carrier gas available at the inlet 11 of the fluid-flow duct 10 and for discharging it towards the outlet 12 of said fluid-flow duct; a bubbler 30 for passing the carrier gas through a volatile liquid 31 contained in the bubbler so as to obtain at the outlet 32 of the bubbler a stream of carrier gas 33 charged with vapor of the liquid; a device 40 for fractioning the charged gas stream obtained at the outlet 32 of the bubbler 30 so as to deliver the charged gas stream in fractioned form via its own outlet 41; and a treatment member 50 for treating the fractioned charged gas stream so as to impart a determined quality thereto prior to ejection via the outlet 12 of the fluid-flow duct 10.

In the meaning of the present description, the term "suction fan" covers any device, regardless of the way in which it operates and regardless of its structure, that is suitable for sucking in a gas via a first point of a circuit and for discharging it via a second point for the purpose of obtaining a flow of said gas, i.e. not only a fan proper, but also, for example: a turbine, a blower, a pump, etc.

Similarly, in the meaning of the present description, the term "bubbler" should be understood as covering any device serving to allow a gas to pass through a liquid and, on passing therethrough, to become charged with vapor of said liquid, with this applying at any appropriate temperature and/or pressure and in any manner whatsoever, regardless of whether the liquid is static and/or dynamic as for example with the liquid being dispensed in drip form or the like.

Figure 2:
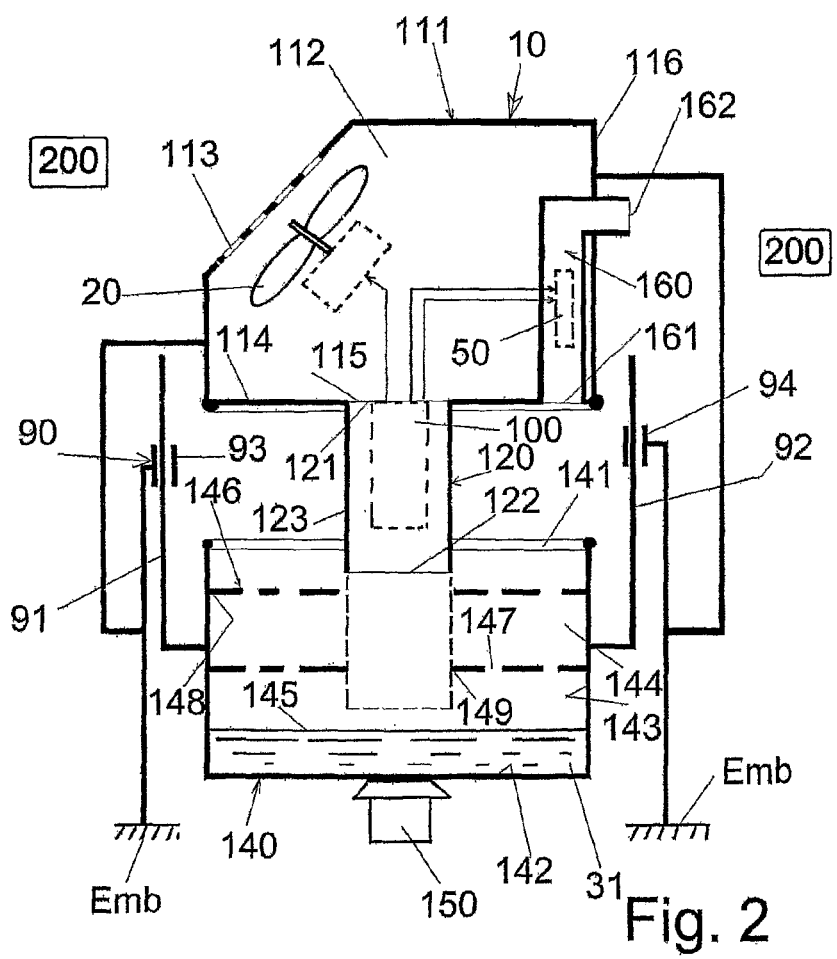
FIG. 2 is a diagrammatic view of a preferred embodiment of apparatus of the invention.
Figure 3:
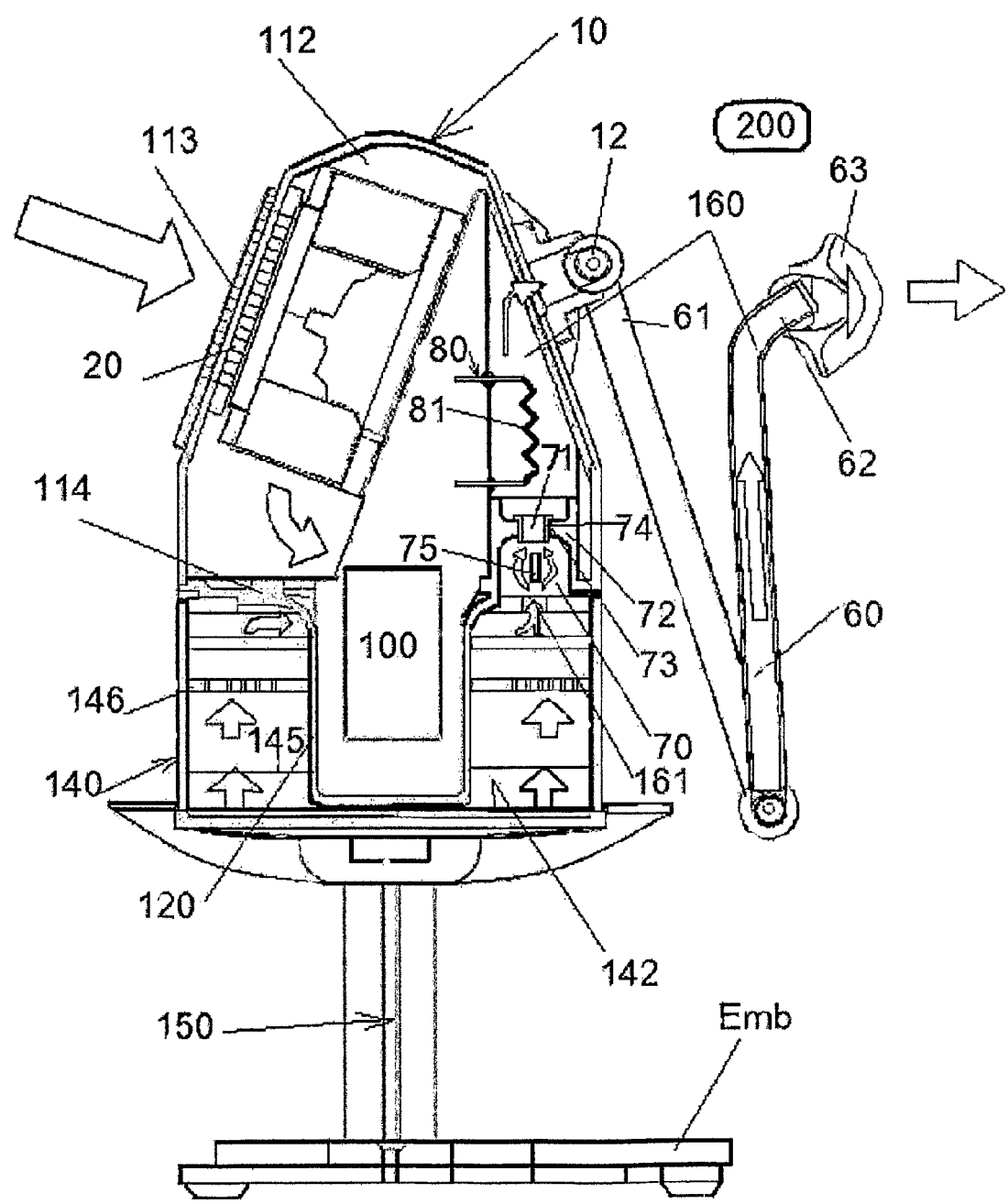
FIGS. 3 and 4 are respectively two orthogonal section views of a manufactured embodiment of the apparatus of the invention complying with the diagram of FIG. 2.
Figure 4:
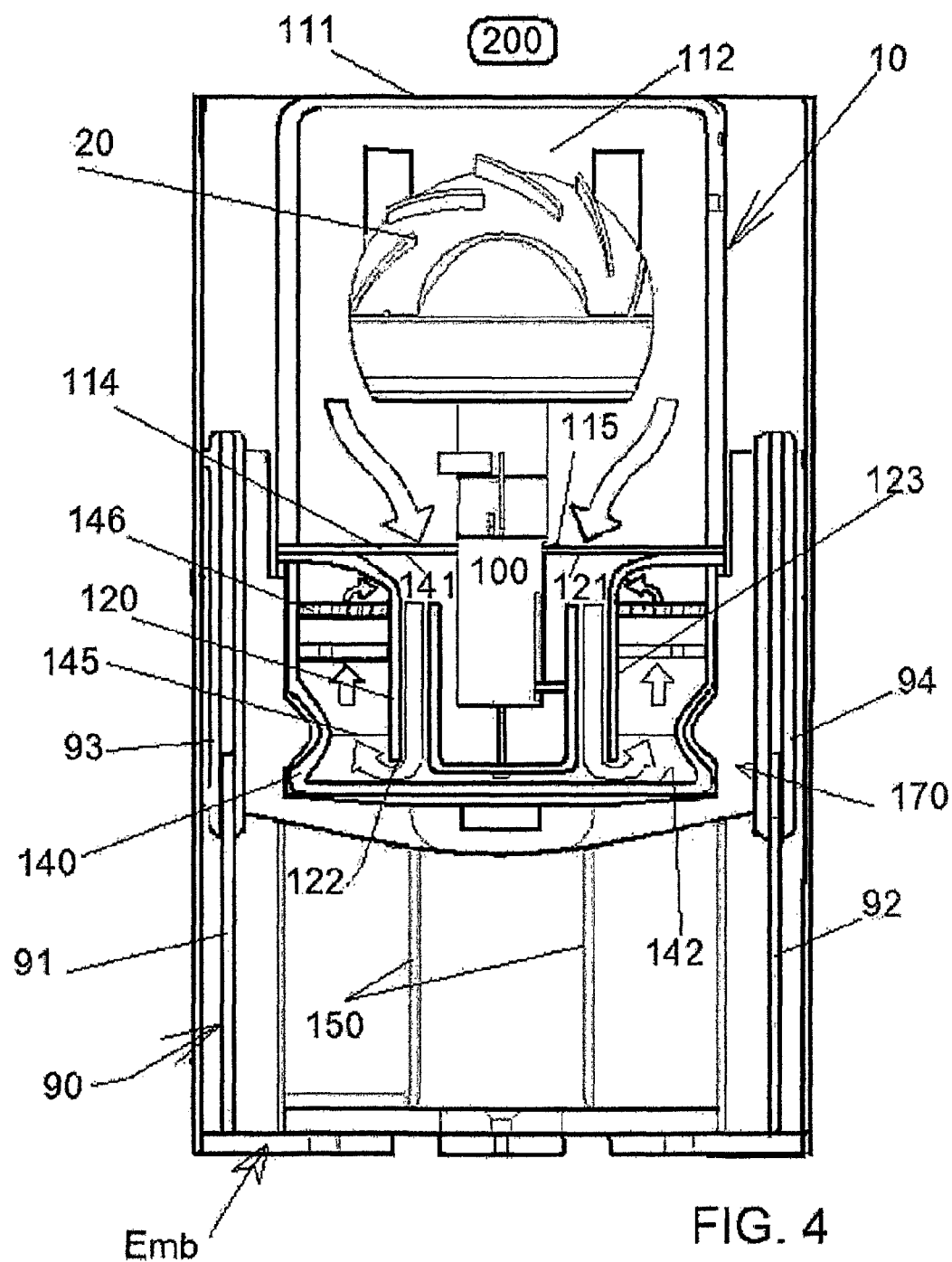

In a preferred embodiment as shown diagrammatically in FIG. 2 and in the manufactured embodiment shown in FIGS. 3 and 4, the fluid flow duct 10 comprises at least one enclosure 111 suitable for being positioned vertically, having both a first opening 113 situated substantially in its top portion 112, said first opening constituting the inlet 11 of the fluid-flow duct 10, and a relatively plane bottom 114 having at least one second opening 115 formed therein, substantially in its center.

The fluid-flow duct 10 further includes a tube 120 that is advantageously substantially vertical as shown, extending, over a vertical height equal to "L", and having at its respective ends firstly a third opening 121 situated in the high position and a fourth opening 122 situated in the low position, the tube 120 being secured to the bottom 114 of the enclosure 111 in such a manner that the second and third openings 115 and 121 are in leaktight communication.

The fluid-flow duct 10 also includes a flask 140 having in its top portion a fifth opening 141 of shape substantially complementary to the bottom 114 of the enclosure 111, the flask having a depth in the vertical direction that is greater than the height L" of the tube 120, and an outlet channel 160 with sixth and seventh openings 161 and 162, the outlet channel being mounted to co-operate with the enclosure 111 and the flask 140 in such a manner that the sixth opening 161 is suitable for being in leaktight communication with the fifth opening 141, e.g. by using an annular gasket or the like as sketched in FIGS. 2 to 4, and that the seventh opening 162 opens out into the ambient medium 200, this seventh opening 160 constituting the outlet 12 of the fluid-flow duct 10.

The description above makes use of the concept of verticality for the enclosure and the tube. Nevertheless, although that defines a preferred configuration, this notion of verticality should not be taken as a limitation on the positioning of the enclosure and the tube, but rather as a way of simplifying the description when defining the various levels, in particular of the openings.

In preferred manner, and as can be seen more particularly in the diagrammatic illustrations of FIGS. 2 to 4, the apparatus further includes means 150 for controlling movement of the flask 140 between first and second stable positions, the first position being a position in which the fifth opening 141 of the flask is spaced apart from the bottom 114 of the enclosure 111 (FIG. 2), and the second position being a position in which the fifth opening 141 of the flask 140 substantially coincides in leaktight manner with said bottom 114 (FIGS. 3 and 4), in such a manner that the tube 120 dips into the flask 140 without reaching its bottom 142 so as to leave a non-zero distance between its fourth opening 122 and the bottom 142 of the flask for a purpose that is explained below, and also so that an annular space 144 is defined between the outer side wall 123 of the tube 120 and the inner side wall 143 of the flask 140 for the purpose of housing a component element of the apparatus of the invention, as is likewise defined below.

These means 150 for controlling the movement of the flask 140 may be of any type, e.g. manual using a lever or the like, however they could also be constituted by a system suitable for being controlled electrically, e.g. an actuator or the like.

In most advantageous manner, when the fluid-flow duct 10 has a structure as defined above, the suction fan 20 is mounted in the enclosure to co-operate with the first opening 113, e.g. immediately facing said opening 113, so as to suck the carrier gas in through this first opening 113 and discharge it via the second opening 115.

The bubbler 30 is constituted by the bottom portion of the flask 140 that is suitable for containing a quantity of volatile liquid 31 that is determined so that the level 145 of the volatile liquid is above the level of the fourth opening 122 of the tube 120 when the flask 140 is in its second position, i.e. above the horizontal plane that contains said opening 122.

The fractioning device 40 placed in the above-defined annular space 144 is advantageously constituted by at least one annular disk 146 including a plurality of holes 147 and a central orifice 149 of section complementary to the section of the outer side wall 123 of the tube 120 so that the tube 120 passes through the annular disk 146 via said central orifice 149.

The disk 146 is shown in FIG. 2 with its outer edge 148 secured to the inner side wall 143 of the flask 140. However it is advantageously mounted so as to be secured either to the enclosure 111 or to the tube 120 (FIGS. 3 and 4) in releasable manner so as to be easily cleaned and so as to avoid hindering filling of the flask 140 in the manner explained below. Under such circumstances, there exists a small gap between its outer edge 148 and the inner side wall 143 of the flask.

The treatment member 50 is placed in the outlet channel 160 (FIGS. 2 and 3), said outlet channel 160 and the treatment member 50 not being visible in FIG. 4 since they are located in particular behind the suction fan 20 and the electrical power supply 100 that is mentioned below.

Advantageously, in order to obtain an apparatus that is as compact as possible, the outlet channel 160 is defined in the enclosure 111 (FIGS. 2 and 3) in such a manner that the sixth opening 161 is made in the bottom 114 of the enclosure 111, the outlet channel 160 passing through the side wall 116 of the enclosure in such a manner that the seventh opening 162 is situated outside the enclosure 111 in the ambient medium 200 so as to open out therein.

Preferably, the outlet channel 160 is situated inside the enclosure in such a manner that its side wall is immersed in the carrier gas stream set into motion by the suction fan 20.

In one possible embodiment, the treatment member 50 for treating the fractioned charged gas stream so as to impart a determined quality thereto prior to it being ejected through the outlet of the fluid-flow duct 10 is constituted by at least one of the following elements: an electric arc generator 70 having at least two electrodes suitable for producing electric discharges; a heat generator 80; and an ultraviolet radiation generator.

In an embodiment with an electric arc generator 70 having at least two electrodes suitable for producing electric discharges, the generator includes (FIG. 3) a fluid-flow constriction 71 constituted by a sleeve 72 having a central passage 73 that is made of an electrically insulating material and that is positioned on the axis of the outlet channel 160 in leaktight manner on the inner side wall of the outlet channel 160. The electric arc generator 70 also includes both a central core 74 made of an electrically-conductive material lining the central passage of the sleeve, the central core 74 constituting one of the two electrodes, and a central electrical terminal 75 positioned in the outlet channel 160 upstream from the central passage 73 so as to be electrically isolated from the outlet channel 160 and positioned at a determined non-zero distance from the central core 74, said central electrical terminal 75 constituting the other electrode, with the electric arc being liable to be struck in conventional manner between these two electrodes 74 and 75.

In an embodiment with a heat generator 80, the generator is advantageously constituted by an electrical resistance 81 placed in the outlet channel 160 (FIG. 3). Nevertheless, the heat generator may be coupled with the electric arc generator 70 as shown in FIG. 3. Under such circumstances, the electrical resistance 81 is positioned downstream from the central passage 73.

Advantageously, the apparatus further includes guide means 90 for guiding the movement of the flask 140 as it passes from its first position to the second, and vice versa, e.g. under drive from the above-defined means 150 for controlling its movement.

In a preferred embodiment, these guide means 90 for guiding the movement of the flask 140 are constituted (FIGS. 2 and 4) by at least two tabs 91 and 92 that are secured to one of the two elements constituted by the flask 140 and the enclosure 111, and by two slideways 93 and 94 in which the two tabs 91 and 92 are suitable for sliding and that are secured respectively to the other one of the two elements constituted by the enclosure 111 and the flask 140.

In the embodiment shown in FIG. 2, the two tabs 91 and 92 are secured to the flask 140 and the two slideways 93 and 94 are secured to the enclosure 111 which is itself secured to a stand Emb, for example.

In the manufactured embodiment shown in FIG. 4, the tabs 91 and 92 are secured to the stand Emb and the two slideways 93 and 94 are secured to the flask via a receiver plate 170 in which the flask 140 is contained. By way of example, this embodiment makes it possible to obtain the movement of the flask between its first and second positions, and also to extract it from the receiver plate 170, in particular for the purpose of cleaning it after each use and/or of filling it in complete safety with the volatile liquid 31 as described above.

The volatile liquid 31 is advantageously a terpene derivative of oleoresins.

Preferably, the carrier gas that is suitable for being sucked in through the first opening 113 is the air present in the ambient medium 200, however it could be any other gas having a source connected to the first opening 113.

Advantageously, the apparatus includes an electrical power supply 100 for powering at least one of the following elements: the suction fan 20; the means 150 for controlling the movement of the flask 140; and the treatment member 50 for treating the fractioned charged gas stream. This electrical power supply may be constituted, for example, by a transformer or the like and it may be connected to the mains or to an independent source such as a battery or the like.

In most advantageous manner, the electrical power supply 100 is positioned inside the tube 120, thereby enabling heat to be exchanged between the power supply and the carrier gas: the gas cools the power supply while the power supply begins the heating of the carrier gas before it passes through the bubbler in order to become charged with the volatile compound.

This apparatus is used mainly for performing intermediate peroxidizing reactions that enable catalysts to be produced for various purposes, e.g. for inhalation. Thus, it is advantageous for the apparatus also to include an articulated pipe 60 (FIG. 3) having one end 61 connected to the outlet 12 from the fluid-flow duct 10 and a breathing endpiece 63 connected to the other end 62 of the pipe 60.

Such an apparatus operates and is used in the manner described below, more particularly for the purpose of inhalation:

Firstly, the flask 140 is taken to its first position and is filled with a previously-defined determined quantity of one of the above-mentioned volatile liquids 31.

Thereafter the flask 140 is taken to its second position and the suction fan 20 is put into operation. A flow of carrier gas is then established, generally a flow of ambient air, that penetrates into the fluid-flow circuit 10 via the opening 113 and follows the path defined in FIGS. 3 and 4 by wide arrows. The carrier gas passes through the bubbler 30 where it becomes charged with vapor of the volatile liquid 31, and the charged gas stream is fractioned on passing via the pierced disk(s) 146 so as to constitute a charged stream in a distribution that is as uniform as possible.

Thereafter the fractioned charged gas stream passes through the outlet channel 160 where it is treated, e.g. as described in the prior document mentioned in the introduction of the present description. It contains little or no non-transformed vapors of oleoresin terpene derivatives, and little or no undesirable ozone derivatives.

This purified fractioned charged gas stream is then ejected via the outlet 12 of the fluid-flow circuit 10 into the ambient medium 200. It may also be sucked out via the pipe 60 and the breathing endpiece 63 by a person who is to inhale it.

The invention claimed is:

1. Apparatus for producing a gas charged with a volatile compound, the apparatus comprising:

a fluid-flow duct (10) having an inlet (11) and an outlet (12), and mounted in succession in series in said fluid-flow duct (10) between its inlet (11) and its outlet (12):

a suction fan (20) for sucking in a carrier gas available at the inlet (11) of the fluid-flow duct (10) and for discharging it towards the outlet (12) of said fluid-flow duct (10);

a bubbler (30) suitable for causing the carrier gas to pass through a volatile liquid (31) suitable for being contained in said bubbler so as to obtain at the outlet (32) of the bubbler a stream of carrier gas (33) charged with vapor of said volatile liquid;

a fractioning device (40) for fractioning said charged gas stream obtained at the outlet (32) of said bubbler (30) so as to deliver at its outlet (41) said charged gas stream in fractioned form; and a treatment member (50) for treating said fractioned charged gas stream to impart a determined quality thereto prior to it being ejected from the outlet (12) of the fluid-flow duct (10);

said fluid-flow duct (10) comprising at least:

an enclosure (111) suitable for being positioned vertically, having both a first opening (113) situated substantially in its top portion (112), said first opening constituting the inlet (11) of the fluid-flow duct (10), and a relatively planar bottom (114) having at least one second opening (115) formed therein;

a tube (120) having a vertical height, having at its two ends respectively a third opening (121) situated in a high position and a fourth opening (122) situated in a low position, said tube (120) being secured to said bottom (114) of said enclosure (111) in such a manner that the second and third openings (115, 121) are in leaktight communication;

a flask (140) having in its upper portion a fifth opening (141) of a shape that is substantially complementary to the bottom (114) of said enclosure (111), said flask having a depth in the vertical direction that is greater than the of the tube (120); and an outlet channel (160) having sixth and seventh openings (161, 162), said outlet channel being mounted to co-operate with said enclosure (111) and said flask (140) in such a manner that the sixth opening (161) is suitable for being in leaktight communication with the fifth opening (141), and that the seventh opening (162) opens out into the ambient medium (200), said seventh opening (160) constituting the outlet (12) of said fluid-flow duct (10).

2. Apparatus according to claim 1, further comprising means (150) for controlling the movement of said flask (140) between first and second stable positions, the first position being a position in which the fifth opening (141) of the flask is spaced apart from the bottom (114) of said enclosure (111), and the second position being a position in which said fifth opening (141) of the flask (140) substantially coincides in leaktight manner with the bottom (114) of said enclosure (111), in such a manner that the tube (120) dips into said flask (140) without reaching its bottom (142) so as to leave a non-zero distance between its fourth opening (122) and the bottom (142) of the flask, and also in such a manner as to define an annular space (144) between the outer side wall (123) of the tube (120) and the inner side wall (143) of the flask (140).

3. Apparatus according to claim 2, wherein:

said suction fan (20) is mounted in said enclosure to co-operate with said first opening (113) to suck the carrier gas in through said first opening (113) and to discharge it through the second opening (115);

said bubbler (30) is constituted by the bottom portion of the flask (140) that is suitable for containing a determined quantity of volatile liquid (31) so that the level (145) of said volatile liquid is higher than the level of the fourth opening (122) of the tube (120) when the flask (140) is in its second position;

said fractioning device (40) located in the annular space (144) is constituted by at least one annular disk (146) including a plurality of holes (147), and a central orifice (149) of section complementary to the section of the outer side wall (123) of the tube (120), the tube (120) passing through said central orifice; and said treatment member (50) is disposed in said outlet channel (160).

4. Apparatus according to claim 1, wherein the outlet channel (160) is defined in said enclosure (111) in such a manner that the sixth opening (161) is formed in the bottom (114) of said enclosure (111), the outlet channel (160) passing through the side wall (116) of the enclosure in such a manner that the seventh opening (162) is situated outside said enclosure (111) in the ambient medium (200).

5. Apparatus according to claim 1, wherein said treatment member (50) for treating said fractioned charged gas stream so as to impart a determined quality thereto prior to it being ejected through the outlet of the fluid-flow duct (10) is constituted by at least one of the following elements: an electric arc generator (70) having at least two electrodes; a heat generator (80); and an ultraviolet radiation generator.

6. Apparatus according to claim 5, wherein said electric arc generator (70) having at least two electrodes includes both a fluid-flow constriction (71) constituted by a sleeve (72) that has a central passage (73), that is made of an electrically-insulating material, and that is positioned coaxially and in leaktight manner against the inner side wall of the outlet channel (160) in such a manner that said fractioned charged stream passes through the central passage (73) of said sleeve (72), a central core (74) of an electrically-conductive material lining the central passage of the sleeve, said central core constituting one of the two electrodes, and a central electrical terminal (75) positioned in said outlet channel (160) upstream from said central passage (73) in such a manner as to be electrically isolated from said outlet channel (160) and to be positioned at a determined non-zero distance from the central core (74), said central electrical terminal (75) constituting the other electrode.

7. Apparatus according to claim 5, wherein said heat generator (80) is constituted by an electrical resistance (81).

8. Apparatus according to claim 2, further comprising it includes guide means (90) for guiding the movement of said flask (140) between its first and second stable positions.

9. Apparatus according to claim 8, wherein the guide means (90) for guiding the movement of said flask are constituted by at least two tabs (91, 92) that are secured to one of the two elements constituted by the flask (140) and the enclosure (111), and by two slideways (93, 94) in which the two tabs (91, 92) are suitable for sliding and that are secured respectively to the other one of the two elements constituted by the enclosure (111) and the flask (140).

10. Apparatus according to claim 1, further comprising it includes an electrical power supply (100) for powering at least one of the following elements: the suction fan (20); the control means (150) for controlling the movement of the flask (140); and the treatment member (50); the electrical power supply (100) being positioned in the tube (120).

11. Apparatus according to claim 1, further comprising it further includes a hinged pipe (60) having one end (61) connected to the outlet (12) of the fluid-flow duct (10), and having a breathing endpiece (63) connected to the other end (62) of said pipe.

12. Apparatus according to claim 1, wherein said volatile liquid is an essence of oleoresin terpene derivatives, and the carrier gas is ambient air.

13. Apparatus according to claim 2, wherein the outlet channel (160) is defined in said enclosure (111) in such a manner that the sixth opening (161) is formed in the bottom (114) of said enclosure (111), the outlet channel (160) passing through the side wall (116) of the enclosure in such a manner that the seventh opening (162) is situated outside said enclosure (111) in the ambient medium (200).

14. Apparatus according to claim 2, wherein said treatment member (50) for treating said fractioned charged gas stream so as to impart a determined quality thereto prior to it being ejected through the outlet of the fluid-flow duct (10) is constituted by at least one of the following elements: an electric arc generator (70) having at least two electrodes; a heat generator (80); and an ultraviolet radiation generator.

15. Apparatus according to claim 6, wherein heat generator (80) is constituted by an electrical resistance (81).

16. Apparatus according to claim 3, further comprising guide means (90) for guiding the movement of said flask (140) between its first and second stable positions.

17. Apparatus according to claim 2, further comprising an electrical power supply (100) for powering at least one of the following elements: the suction fan (20); the control means (150) for controlling the movement of the flask (140); and the treatment member (50); the electrical power supply (100) being positioned in the tube (120).

\* \* \* \* \*